(12) United States Patent
Chiou et al.

(10) Patent No.: US 11,920,157 B2
(45) Date of Patent: Mar. 5, 2024

(54) APPLICATIONS OF BUTYLIDENEPHTHALIDE

(71) Applicant: NATIONAL DONG HWA UNIVERSITY, Hualien County (TW)

(72) Inventors: Tzyy-Wen Chiou, Hualien County (TW); Shinn-Zong Lin, Taichung (TW); Horng-Jyh Harn, New Taipei (TW); Hong-Lin Su, Taichung (TW); Shih-Ping Liu, Taichung (TW); Kang-Yun Lu, Taichung (TW); Jeanne Hsieh, Hualien (TW)

(73) Assignee: NATIONAL DONG HWA UNIVERSITY, Hualien County (TW)

( * ) Notice: Subject to any disclaimer, the term of this patent is extended or adjusted under 35 U.S.C. 154(b) by 0 days.

(21) Appl. No.: 17/932,549

(22) Filed: Sep. 15, 2022

(65) Prior Publication Data

US 2023/0023270 A1    Jan. 26, 2023

Related U.S. Application Data

(62) Division of application No. 16/093,950, filed as application No. PCT/CN2017/082838 on May 3, 2017, now abandoned.

(60) Provisional application No. 62/339,506, filed on May 20, 2016.

(51) Int. Cl.
| | |
|---|---|
| *C12N 5/077* | (2010.01) |
| *A61K 31/341* | (2006.01) |
| *A61K 35/28* | (2015.01) |
| *A61K 35/35* | (2015.01) |
| *A61P 3/04* | (2006.01) |

(52) U.S. Cl.
CPC .......... *C12N 5/0653* (2013.01); *A61K 31/341* (2013.01); *A61K 35/28* (2013.01); *A61K 35/35* (2013.01); *A61P 3/04* (2018.01); *C12N 2501/33* (2013.01); *C12N 2501/999* (2013.01)

(58) Field of Classification Search
None
See application file for complete search history.

(56) References Cited

U.S. PATENT DOCUMENTS

| | | |
|---|---|---|
| 2007/0042057 A1 | 2/2007 | Raederstorff et al. |
| 2007/0082947 A1 | 4/2007 | D'Orazio et al. |
| 2007/0092551 A1 | 4/2007 | Enoki et al. |
| 2009/0192218 A1 | 7/2009 | D'Orazio et al. |
| 2014/0212970 A1 | 7/2014 | Liu et al. |
| 2015/0030662 A1 | 1/2015 | Raghunath et al. |

FOREIGN PATENT DOCUMENTS

| | | |
|---|---|---|
| CN | 1856303 | 11/2006 |
| CN | 104350146 | 2/2015 |
| JP | 2006-528666 | 12/2006 |
| JP | 2012-135261 | 7/2012 |
| JP | 2014-065672 | 4/2014 |
| JP | 2014-620531 | 8/2014 |
| TW | 201430134 | 8/2014 |
| WO | 2004-096198 | 11/2004 |
| WO | 2013003595 | 1/2013 |

OTHER PUBLICATIONS

Brindis et al. "(Z)-3-Butylidenephthalide from Ligusticum porteri, an alpha-Glucosidase Inhibitor" (2011), vol. 74: 314-320. (Year: 2011).*
Benenuti et al. "Rosiglitazone stimulates adipogenesis and decreases osteoblastogenesis in human mesenchymal stem cells" 2007 , J Endocrin Invest, vol. 30: RC26-RC30. (Year: 2007).
Brindis, F. et al., "(Z)-3-Butylidenephthalide from Ligusticum porteri, an r-Glucosidase Inhibitor," Journal of Natural Products, 2011, vol. 74, pp. 314-320.
Harms, M. et al., "Brown and beige fat: development, function and therapeutic potential," Nature Medicine, 2013, vol. 19(10), pp. 1242-1263.
Bacha, F. et al. "Cardiac Abnormalities in Youth with Obesity and Type 2 Diabetes," Curr. Diab. Rep., 2016, vol. 16, pp. 1-9.
Chrostowska, M. et al., "Impact of obesity on cardiovascular health," Best Practice & Research Clinical Endocrinology & Metabolism, 2013, vol. 27, pp. 147-156.
Barton, M. et al., "Obesity and risk of vascular disease: importance of endothelium-dependent vasoconstriction," British Journal of Pharmacology, 2012, vol. 165, pp. 591-602.
Mount, P. et al., "Obesity-Related Chronic Kidney Disease—The Role of Lipid Metabolism," Metabolites, 2015, vol. 5, pp. 720-732.
International Search Report of International Application No. PCT/CN217 /082838 dated Aug. 1, 2017.
File history of U.S. Appl. No. 16/093,950, filed Oct. 15, 2018.
Yan, Liang-Jun, The Nicotinamide/Streptozotocin Rodent Model of Type 2 Diabetes Renal Pathophysiology and Redox Imbalance Features, Biomolecules, 2022, 12, 1225 (16 pages).
Furman, Brian L., Streptozotocin-Induced Diabetic Models in Mice and Rats, Current Protocols, (2021) edition 78, vol. 1, (22 pages).
Yi, Wei, et al., Reduced Cardioprotective Action of Adiponectin in High-fat Diet-Induced Type II Diabetic Mice and Its Underlying Mechanisms, Antioxidants & Redox Signaling Forum Original Research Communication, (2011) No. 7, vol. 15, (10 pages).
Jiaxun, Lu et al., Less fat is better? It must be at least 15% of your body weightl. website, https://www.commonhealth.com.tw/, Mar. 4, 2015, (8 pages).

* cited by examiner

*Primary Examiner* — Teresa E Knight
(74) *Attorney, Agent, or Firm* — Ping Wang; Rimon Law

(57) ABSTRACT

Applications of butylidenephthalide (BP), comprising the use of BP in providing a kit for promoting differentiation of stem cells into brown adipose cells, and the use of BP in preparing a medicament, wherein the medicament is used for inhibiting the accumulation of white adipose cells, promoting the conversion of white adipose cells into brown adipose cells, inhibiting weight gain and/or reducing the content of triglycerides, glucose, and total cholesterol in blood.

12 Claims, 10 Drawing Sheets

APPLICATIONS OF BUTYLIDENEPHTHALIDE

This application is a Divisional application of application Ser. No. 16/093,950, filed Oct. 15, 2018, which is a national stage application of International Patent Application No. PCT/CN2017/082838, filed Mar. 5, 2017, which claims the benefit of U.S. Provisional Application Ser. No. 62/339,506, filed May 20, 2016. The entirety of the aforementioned applications is incorporated herein by reference.

FIELD

The present invention relates to the use of butylidenephthalide (BP), especially relates to the use of butylidenephthalide (BP) in promoting the differentiation of a stem cell into a brown-like adipose cell and the use of butylidenephthalide (BP) in inhibiting the accumulation of white fat, promoting the conversion of white fat into brown fat, inhibiting weight gain and/or reducing the contents of triglycerides, glucose and total cholesterol in blood. By administering butylidenephthalide (BP) in combination with a mesenchymal stem cell and/or a brown-like adipose cell to a subject, better efficiencies on inhibiting weight gain, reducing the accumulation of adipose tissue and promoting the conversion of white fat into brown fat in the subject can be provided.

BACKGROUND

Fat can be roughly classified into two types: white fat and brown fat. The appearance of white fat, which consists of white adipose cells, is of white color; while the appearance of brown fat, which consists of brown adipose cells, is of brown color. White adipose cell differentiated from Myf-5 negative myofibroblast is characterized by containing a single and large adipose droplet on morphology, and its main function is to store energy. Brown adipose cell differentiated from Myf-5 positive myofibroblast is characterized by containing numerous small adipose droplets dispersed therein and a large number of mitochondria. The brown adipose cell can also highly express uncoupling protein 1 (UCP1), and its main function is to metabolize energy.

With factors such as a Western diet culture that is high in oil, sugar and fat, a lifestyle generally lacking in exercise, and heredity, obesity has become a worldwide health problem. It is noticed from researches that characteristics such as the accumulation of body white fat and the excess contents of triglycerides, glucose and total cholesterol in blood are often present in a subject with obesity. The occurrences of metabolic syndrome such as diabetes mellitus, cardiovascular disease, cerebrovascular disease, hypertension and nephropathy are also closely related to high triglycerides, hyperglycemia and high cholesterol. Though there are many commercially available drugs being alleged to be able to reduce or control weight, most of those drugs achieve the alleged purposes by the mechanisms such as increasing the feeling of satiety, inhibiting appetite and inhibiting the absorption of fat. Accordingly, the administration of those drugs is often accompanied by many side effects such as headache, hypoglycemia, constipation, insomnia, and oily feces, and may even increase the risk of getting heart disease and stroke. Therefore, there is still a need in the art for developing a method or drug that has fewer side effects and is effective in anti-obesity and preventing metabolic syndrome associated with obesity.

Researches have shown that though brown fat is only about 0.1% of the weight of an adult, it burns about 10~20% of the daily basal metabolic rate and is effective in accelerating the clearance of triglycerides, ameliorating the hyperactivity of insulin, and anti-obesity. Therefore, the researches of investigating anti-obesity and preventing metabolic syndrome associated with obesity have paid more and more attention to the issue of how to increasing the proportion of body brown fat.

It is known that there are two approaches for increasing the proportion of brown fat in an animal body, one is to promote the conversion of white fat into brown fat in the animal body (referred to as "fat browning"), and the other is to inject a cell suspension of brown adipose cells or brown-like adipose cells to the animal (referred to as "cell infusion of brown adipose cells" or "cell infusion of brown-like adipose cells"). The brown-like adipose cell refers to a cell that has the morphology of a brown adipose cell characterized by containing numerous small adipose droplets dispersed therein, containing a large number of mitochondria, and having highly expressed UCP1 protein, but is different from a brown adipose cell in the gene expression. It is known that a brown-like adipose cell can be obtained by inducing and promoting the differentiation of a stem cell or the conversion of a white adipose cell. Because brown-like adipose cell is similar to brown adipose cell on cell morphology, it is deemed as belonging to brown fat in fat classification.

However, so far, there is still a lack of effective technical means for the aforementioned two approaches of increasing the proportion of body brown fat. Though researches have shown that exercise or cold environments are effective in stimulating the occurrence of fat browning in an animal body, many people are generally lacking in exercise and cold environments are not readily available. It is impractical to effectively and stably promote the fat browning in an animal body through exercises or the exposure to cold environments. In addition, the cell infusion of brown-like adipose cells/brown adipose cells is not cost-effective because the source of brown-like adipose cells/brown adipose cells is rare and the cost for obtaining the cells is high.

In view of the above issues, there is a necessity and urgency for developing an effective method for promoting the fat browning in an animal body and/or solving the problem of the difficulty of obtaining brown-like adipose cells/brown adipose cells. Inventors of the present invention discovered that a conditional medium, which comprises a basic medium and an ingredient capable of inducing the differentiation of a stem cell into an adipose cell, when being externally added with butylidenephthalide (BP), can effectively promote the differentiation of a stem cell into a brown-like adipose cell. As a result, the cost for obtaining brown-like adipose cells can be reduced, and the problem of the difficulty of obtaining brown-like adipose cells/brown adipose cells can be solved.

Inventors of the present invention also discovered that the administration of butylidenephthalide (BP) alone and the administration of butylidenephthalide (BP) in combination with mesenchymal stem cells and/or brown-like adipose cells to an animal can both effectively inhibit the accumulation of white fat, promote the conversion of white fat into brown fat, inhibit weight gain and/or reduce the contents of triglycerides, glucose and total cholesterol in blood. Accordingly, the use of butylidenephthalide (BP) can promote the fat browning in an animal body so as to achieve the effects of anti-obesity and prevent metabolic syndrome associated with obesity, and can avoid the side effects caused by the commercially available anti-obesity drugs that achieve the anti-obesity purpose by the mechanisms such as increasing the feeling of satiety, inhibiting appetite, and inhibiting the absorption of fat.

SUMMARY

An objective of the present invention is to provide a kit for promoting the differentiation of a stem cell to into a brown-like adipose cell, comprising the following components: (1) a conditional medium, comprising a basic medium and an ingredient capable of inducing the differentiation of a stem cell into an adipose cell; and (2) butylidenephthalide (BP). Preferably, the ingredient is rosiglitazone, insulin, 3-isobutyl-1-methylxanthine (IBMX), dexamethasone, and combinations thereof.

Another objective of the present invention is to provide a use of butylidenephthalide (BP) in the manufacture of a medicament, wherein the medicament is used for inhibiting the accumulation of white fat, promoting the conversion of white fat into brown fat, inhibiting weight gain and/or reducing the contents of triglycerides, glucose and total cholesterol in blood. Particularly, the medicament is used for anti-obesity and/or preventing metabolic syndrome associated with obesity. Preferably, the medicament is administered in combination with at least one of a mesenchymal stem cell and a brown-like adipose cell. More preferably, the medicament is administered in combination with an adipose stem cell. The medicament is administered at an amount ranging from about 30 mg (as BP)/kg-body weight to about 2000 mg (as BP)/kg-body weight per day.

Still another objective of the present invention is to provide a method for inhibiting the accumulation of white fat, promoting the conversion of white fat into brown fat, inhibiting weight gain and/or reducing the contents of triglycerides, glucose and total cholesterol in blood, comprising administering to a subject in need an effective amount of butylidenephthalide (BP). Particularly, the method is for anti-obesity and/or preventing metabolic syndrome associated with obesity. The metabolic syndrome is at least one of diabetes mellitus, cerebrovascular disease, cardiovascular disease, hypertension and nephropathy. Preferably, the subject in need is administered with an effective amount of butylidenephthalide (BP) and at least one of a mesenchymal stem cell and a brown-like adipose cell. More preferably, the subject in need is administered with an effective amount of butylidenephthalide (BP) and an adipose stem cell. The amount of bytulidenephthalide (BP) is ranging from about 30 mg (as BP)/kg-body weight to about 2000 mg (as BP)/kg-body weight per day.

BRIEF DESCRIPTION OF THE DRAWINGS

FIGS. 2A and 2B shows the contents of adipose droplets of cells with different treatments, wherein FIG. 2A is a photo of adipose cells stained by oil red dye by observing with a microscope, FIG. 2B is a histogram showing the quantified absorbances of adipose droplets, and FIGS. 2A and 2B both include the results of adipose stem cells (without cultivation in a conditional medium; undifferentiated), adipose cells (cultivated in a conditional medium; differentiated) and adipose cells (differentiated) separately treated by 2, 10 or 50 µg/mL of butylidenephthalide (BP);

FIGS. 3A and 3B show the fat browning effects of butylidenephthalide (BP) at different concentrations, wherein FIG. 3A is a curve diagram showing the effect of different concentrations of butylidenephthalide (BP) on the oxygen consumption rate of adipose cells, FIG. 3B is a histogram showing the effect of different concentrations of butylidenephthalide (BP) on the spare respiratory capacity of adipose cells, and FIGS. 3A and 3B both include the results of undifferentiated adipose stem cells (represented as "A"), differentiated adipose cells (represented as "0"), adipose cells cultivated in a conditional medium that was externally added with butylidenephthalide (BP) (to a final concentration of 2 µg/mL) for 7 days (represented as "2"), adipose cells cultivated in a conditional medium that was externally added with butylidenephthalide (BP) (to a final concentration of 10 µg/mL) for 7 days (represented as "10"), and adipose cells cultivated in a conditional medium that was externally added with butylidenephthalide (BP) (to a final concentration of 50 µg/mL) for 7 days (represented as "50");

FIGS. 4A and 4B show the results of the expression of UCP1 gene in the adipose cell determined by reverse transcription polymerase chain reaction (RT-PCR) and the expression of UCP1 protein in the adipose cell determined by Western blot, wherein FIG. 4A is a photo showing the expression levels of UCP1, FABP4 (the internal control of adipose cells) and Actin (the internal control of all cells) genes, FIG. 4B is a photo showing the expression levels of UCP1, FABP4 and Actin proteins, and FIGS. 4A and 4B both include the results of control group (cultivated in a conditional medium for 14 days; represented as "Control group"), butylidenephthalide (BP)-treated group (cultivated in a conditional medium for 7 days, and then cultivated in a conditional medium that was externally added with BP for another 7 days; represented as "BP"), tofacitinib-treated group (cultivated in a conditional medium for 7 days, and then cultivated in a conditional medium that was externally added with tofacitinib for another 7 days; represented as "Tofacitinib"), adenosine-treated group (cultivated in a conditional medium for 7 days, and then cultivated in a conditional medium that was externally added with adenosine for another 7 days; represented as "Adenosine"), proanthocyanidin-treated group (cultivated in a conditional medium for 7 days, and then cultivated in a conditional medium that was externally added with proanthocyanidin for another 7 days; represented as "Proanthocyanidin");

FIGS. 5A and 5B show the effect of butylidenephthalide (BP) and cell infusion on the morphology of mouse fat, wherein FIG. 5A is a photo showing the result of IHC staining of mouse subcutaneous fat slice and FIG. 5B is a photo showing the result of IHC staining of mouse visceral fat slice; the mice in "ND group" were only fed with a normal diet, those in "HFD group" were only fed with a high fat diet, those in "HFD+BP group" were fed with a high fat diet and administered with butylidenephthalide (BP), those in "HFD+ADSC group" were fed with a high fat diet and administered with adipose stem cells, those in "HFD+BP+ADSC group" were fed with a high fat diet and administered with butylidenephthalide (BP) and adipose stem cells, those in "HFD+BLC group" were fed with a high fat diet and administered with brown-like adipose cells, and those in "HFD+BP+BLC group" were fed with a high fat diet and administered with butylidenephthalide (BP) and brown-like adipose cells;

FIGS. 6A to 6C show the effect of butylidenephthalide (BP) and cell infusion on the accumulation of mouse body fat, wherein FIG. 6A is a photo showing the appearances of the heart, liver, kidney, subcutaneous adipose tissue and visceral adipose tissue, FIG. 6B is a histogram showing the weight of mouse subcutaneous adipose tissue, FIG. 6C is a histogram showing the weight of mouse visceral adipose tissue, and FIGS. 6A, 6B and 6C all include the results of "ND group", "HFD group", "HFD+BP group", "HFD+ADSC group", "HFD+BP+ADSC group", "HFD+BLC group" and "HFD+BP+BLC group";

FIGS. 8A to 8C show the effect of butylidenephthalide (BP) and cell infusion on the mouse serum biochemical values, wherein FIG. 8A is a histogram showing the content of glucose in blood, FIG. 8B is a histogram showing the content of triglycerides in blood, FIG. 8C is a histogram showing the content of total cholesterol in blood, and FIGS. 8A, 8B and 8C all include the results of "ND group", "HFD group", "HFD+BP group", "HFD+ADSC group", "HFD+BP+ADSC group", "HFD+BLC group" and "HFD+BP+BLC group".

DESCRIPTION OF THE PREFERRED EMBODIMENTS

Figure 1:
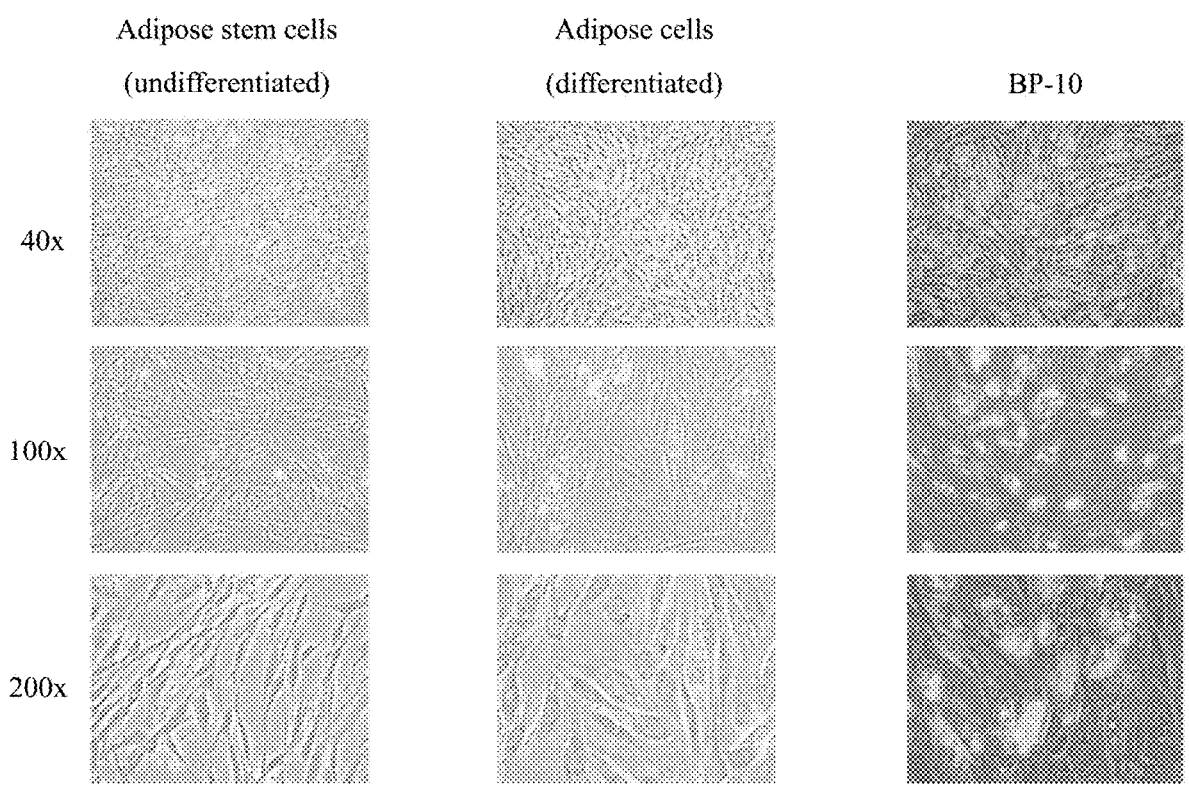
FIG. 1 shows the differentiation process of producing adipose droplets in a stem cell treated by butylidenephthalide (BP), wherein from left to right, each of the microscope photos separately shows the morphology of adipose stem cells, adipose cells differentiated from adipose stem cells and cells obtained from cultivating the adipose cells in a conditional medium that was externally added with butylidenephthalide (BP) in different magnifications (40-fold, 100-fold and 200-fold)

The following paragraphs will describe some of the embodiments of the present invention in detail. However, without departing from the spirit of the present invention, the present invention may be embodied in various embodiments and should not be limited to the embodiments described in the specification and the appended claims. Unless otherwise indicated herein, the expression "a," "an," "the," or the like recited in the specification of the present invention (especially in the claims) are intended to include both the singular and plural forms.

According to the standard of Health Promotion Administration, Ministry of Health and Welfare of Taiwan, the definition of obesity is BMI>24, and the definition of metabolic syndrome is BMI>24, high-density lipoprotein (HDL) cholesterol<50 mg/dL, fasting blood glucose>100 mg/dL and triglycerides>150 mg/dL. In the standard of World Health Organization (WHO), the definition of obesity of European and American races is BMI>30. According to National Cholesterol Education Program Adult Treatment Panel-III (NCEP ATP III) of United State, the definition of metabolic syndrome is a subject having at least three indices of blood pressure>130/85 mmHg, triglycerides>150 mg/dL, HDL cholesterol<40 mg/dL (male) or <50 mg/dL (female), waistline>102 cm (male) or >88 cm (female), and fasting blood glucose>110 mg/dL. Therefore, in the research, high cholesterol, hyperglycemia and high triglycerides are generally used as the indices of obesity.

It is known that the occurrence of metabolic syndrome such as diabetes mellitus, cardiovascular disease, cerebrovascular disease, hypertension and nephropathy is closely associated with obesity. These can be seen in "Cardiac Abnormalities in Youth with Obesity and Type 2 Diabetes. *Curr Diab Rep.* 2016 July; 16(7):62", "Impact of obesity on cardiovascular health. *Best Pract Res Clin Endocrinol Metab.* 2013 April; 27(2):147-156", "Obesity and risk of vascular disease: importance of endothelium-dependent vasoconstriction. *Br J Pharmacol.* 2012 February; 165(3): 591-602", and "Obesity-Related Chronic Kidney Disease—The Role of Lipid Metabolism. Metabolites. 2015 Dec. 11; 5(4):720-732", which are entirely incorporated hereinto by reference.

As described above, the researches of investigating anti-obesity and preventing metabolic syndrome associated with obesity have paid more and more attention to the issue of how to increase the proportion of body brown fat. It has been confirmed by researches that thermogenesis in brown fat can be driven by uncoupling the respiratory chain of mitochondria in cells, wherein with the use of the PET/CT image, it is discovered in adult body that the thermogenesis activity of adipose tissue is positively related to the expression level of UCP1. Specifically, the cells highly expressing UCP1 (including brown adipose cells and brown-like adipose cells) can conduct oxidation through the electron transport chain in uncoupling the respiratory chain of mitochondria, but the cells cannot conduct phosphorylation, and thus ATP will not be produced. This process can promote the consumption of nutrition and oxygen, and thus, can be used for achieving the purpose of weight loss. These can be seen in "Brown and beige fat: development, function and therapeutic potential. *Nat Med.* 2013 October; 19(10):1252-1263, which is entirely incorporated hereinto by reference.

It is known that the approaches of increasing the proportion of body brown fat include promoting the fat browning in an animal body and infusing brown adipose cells and/or brown-like adipose cells. However, as described above, there is neither an effective method for promoting the fat browning in an animal body nor an effective mean for solving the problem of the difficulty of obtaining brown adipose cells and brown-like adipose cells. Though prior researches have shown that drugs such as tofacitinib, adenosine and proanthocyanidin can be used for promoting the differentiation of a stem cell into a brown-like adipose cell, the effect thereof is limited.

Inventors of the present invention discovered that a conditional medium, which comprises a basic medium and an ingredient capable of inducing the differentiation of a stem cell into an adipose cell, being externally added with butylidenephthalide (BP), can effectively promote the differentiation of a stem cell into a brown-like adipose cell.

Therefore, the present invention relates to a kit for promoting the differentiation of a stem cell into a brown-like adipose cell, comprising the following components: (1) a conditional medium, comprising a basic medium and an ingredient capable of inducing the differentiation of a stem cell into an adipose cell, and (2) butyildenephthalide (BP). The use of the kit in accordance with the present invention can effectively promote the differentiation of a stem cell into a brown-like adipose cell and stably provide a large amount of brown-like adipose cells in a cheaper way. The provided brown-like adipose cells not only can be used in the cell infusion of brown-like adipose cells, but also can be used in the investigation related to obesity or energy metabolism. The application range of the brown-like adipose cell is wide.

In the kit provided in accordance with the present invention, any suitable ingredient capable of inducing the differentiation of a stem cell into an adipose cell can be used in component (1) (i.e., a conditional medium) of the kit. For example, the ingredient can be selected from the group consisting of rosiglitazone, insulin, 3-isobutyl-1-methylxanthine (IBMX), dexamethasone, and combinations thereof, but is not limited thereby.

In component (1) of the kit (i.e., a conditional medium) provided in accordance with the present invention, the basic medium comprises the essential ingredient capable of providing nutrition and condition (e.g., pH value and humidity) for stem cell growth, which is generally adjusted depending on the need of the cultivated stem cell. In general, examples of the adoptable basic media include DMEM medium (Dulbecco's Modified Eagle's Medium), MEM medium (Minimum Essential Medium), α-MEM medium, BME medium (Basal Media Eagle), MEM/F12 medium, Ham's F10 medium, Ham's F12 medium, and RPMI medium (Rosewell Park Memorial Institute), but is not limited thereby. In some embodiments of the present invention, DMEM medium was used in the kit.

In the kit in accordance with the present invention, component (1) (i.e., a conditional medium) and component (2) (i.e., butylidenephthalide (BP)) are normally independently packaged and stored, and can be transported or sold separately or in a set. Optionally, the subcomponents in component (1) could be independently packaged and stored. In addition, the kit can further comprise an instruction manual, which provides the procedures and program for the user to mix the components on-site for culturing, treating and using the cells.

For example, when the subcomponents of component (1) and component (2) are independently packaged and stored and transported or sold separately, the ingredient(s) capable of inducing the differentiation of a stem cell into an adipose cell (e.g., rosiglitazone, insulin, 3-isobutyl-1-methylxanthine (IBMX) and dexamethasone) and butylidenephthalide (BP) could be kept in a dark environment at a temperature of less than 4° C., and the basic medium could be kept in an environment at a temperature of −20° C. Also, when the components in the kit in accordance with the present invention are transported and sold in a set, butylidenephthalide (BP) and the ingredient(s) capable of inducing the differentiation of a stem cell into an adipose cell could be kept in a container with an interior temperature of less than 4° C. and the basic medium could be kept in a container with an interior temperature of −20° C. (e.g., an ice box). There is no particular limitation on the shape and size of the containers, as long as the containers can serve the desired insulation function to ensure that the storage temperatures of components will not affect each other when the components are transported and sold in a set.

When using the kit in accordance with the present invention, there is no particular limitation for the order to formulate and mix each component. For example, when the subcomponents of the conditional medium are packaged separately, the conditional medium could be formulated, and then mixed with butylidenephthalide (BP). Also, butylidenephthalide (BP) could be mixed with the basic medium, and then mixed with other subcomponents; or each subcomponent of the conditional medium could be mixed with butylidenephthalide (BP) simultaneously. In addition, butylidenephthalide (BP) can be directly mixed with the conditional medium or basic medium; or butylidenephthalide (BP) can be dissolved in a solvent to provide a butylidenephthalide (BP) solution, and then the butylidenephthalide (BP) solution is mixed with the conditional medium or basic medium. Examples of the solvents capable of dissolving butylidenephthalide (BP) include dimethyl sulfoxide (DMSO), polyoxyethylene castor oil (Kolliphor® EL), ethanol, vegetable oil and animal oil, but is not limited thereby.

It is discovered that when using the kit in accordance with the present invention, butylidenephthalide (BP) at an overly low concentration cannot effectively promote the differentiation of a stem cell into a brown-like adipose cell; however, butylidenephthalide (BP) at an overly high concentration may cause cell damage. Therefore, the used concentration generally ranges from about 1 μg to about 100 μg per mL of a conditional medium, preferably ranges from about 2 μg to about 50 μg per mL of a conditional medium, and more preferably ranges from about 5 μg to about 20 μg per mL of a conditional medium. For example, as shown in the appended examples, butylidenephthalide (BP) can effectively promote the differentiation of a stem cell into a brown-like adipose cell at a concentration of about 10 μg per mL of a conditional medium.

Inventors of the present invention also discovered that the administration of butylidenephthalide (BP) alone and the administration of butylidenephthalide (BP) in combination with mesenchymal stem cells and/or brown-like adipose cells to an animal can both achieve the effects on inhibiting the accumulation of white fat, promoting the conversion of white fat into brown fat, inhibiting weight gain and/or reducing the contents of triglycerides, glucose and total cholesterol in blood.

Therefore, the present invention also relates to a use of butylidenephthalide (BP) in the manufacture of a medicament, wherein the medicament is used for inhibiting the accumulation of white fat, promoting the conversion of white fat into brown fat, inhibiting weight gain and/or reducing the contents of triglycerides, glucose and total cholesterol in blood. The medicament provided in accordance with the present invention especially can be used for anti-obesity and/or preventing metabolic syndrome associated with obesity. The metabolic syndrome associated with obesity is at least one of diabetes mellitus, cerebrovascular disease, cardiovascular disease, hypertension and nephropathy. Optionally, the medicament could be administered in combination with mesenchymal stem cells and/or brown-like adipose cells.

Depending on the desired purpose, the medicament of the present invention could be provided in any suitable form without specific limitations. For example, the medicament could be administered to a subject in need by an oral or parenteral (such as subcutaneous injection, intravenous injection, muscular injection, peritoneal injection, transdermal, subcutaneous implantation or interstitial implantation) route, but is not limited thereby. Particularly, the oral administration can be easily taken by patients themselves on time. Depending on the form and purpose, suitable carriers could be chosen and used to provide the medicament, as long as the carriers do not adversely affect the desired effects of butylidenephthalide (BP). Examples of the carriers include excipients, diluents, auxiliaries, stabilizers, absorbent retarders, disintegrating agent, hydrotropic agents, emulsifiers, antioxidants, adhesives, binders, tackifiers, dispersants, suspending agents, lubricants, hygroscopic agents, etc.

As for a dosage form for oral administration, examples of suitable carriers include, but are not limited to, water, saline, dextrose, glycerol, ethanol or its analogs, cellulose, starch, sugar bentonite, and combinations thereof. The medicament could be provided in any suitable form for oral administration in any suitable way, such as in a solid form of a tablet, a pill, a capsule, granules, a pulvis, or in a liquid form of an oral liquid, a syrup, a spirit, an elixir, a tincture, etc., but is not limited thereby.

As for the form of injection or drip suitable for subcutaneous, intravenous, muscular, or peritoneal administration, the medicament provided in accordance with the present invention could comprise one or more ingredient(s), such as an isotonic solution, a salt-buffered saline (e.g., phosphate-buffered saline or citrate-buffered saline), a hydrotropic agent, an emulsifier, a 5% sugar solution, and other carriers to provide the medicament as an intravenous infusion, an emulsified intravenous infusion, a powder for injection, a suspension for injection, or a powder suspension for injection, etc. Alternatively, the medicament could be prepared as a pre-injection solid. The pre-injection solid could be provided in a form which is soluble in other solutions or suspensions, or in an emulsifiable form. A desired injection is provided by dissolving the pre-injection solid in other solutions or suspensions or emulsifying it prior to being administered to a subject in need. In addition, as for the external dosage form for transdermal administration, the medicament could be provided in a form of such as a liniment (e.g., an emulsion, a cream, a gel, a dispersing paste, an ointment), a spray, a patch, or a solution (e.g., a cleaning liquid, a suspension), etc.

As for a dosage form suitable for subcutaneous implantation or interstitial implantation, the medicament provided in accordance with the present invention could further comprise one or more ingredients, such as an excipient, a stabilizer, a buffer, other carriers, etc., to provide the medicament in a form of such as a wafer, a tablet, a pill, a capsule, and the likes. Therefore, the medicament could be implanted into a subject to slowly and continuously release the butylidenephthalide (BP) contained therein to the tissues surrounding the implanted site, and thus, could achieve a locally stable high dose of medicament for inhibiting the accumulation of white fat, promoting the conversion of white fat into brown fat, inhibiting weight gain and/or reducing the contents of triglycerides, glucose and total cholesterol in blood. For example, the medicament provided in accordance with the present invention could be mixed with p(CPP-SA) copolymer to provide a mixture; the mixture is then dissolved in methylene dichloride and dried to provide a powder; thereafter, the powder is put in a mold and compressed under a slight pressure to provide a wafer for subcutaneous implantation or interstitial implantation, but is not limited thereby.

Optionally, the medicament provided in accordance with the present invention could further comprise a suitable amount of additives, such as a flavoring agent, a toner, or a coloring agent for enhancing the palatability and the visual perception of the medicament, and a buffer, a conservative, a preservative, an antibacterial agent, or an antifungal agent for improving the stability and storability of the medicament. In addition, the medicament could optionally further comprise one or more other active ingredients such as β-adrenaline receptor agonists (e.g., CL316,243), PPAR-γ agonists (e.g., rosiglitazone), metabolic promotion related factors (e.g., adiponectin), immunomodulators, etc., or be used in combination with a medicament comprising one or more other active ingredients, to further enhance the effect of the medicament, or to increase the application flexibility and adaptability of the preparation thus provided, as long as the other active ingredients do not adversely affect the desired effects of butylidenephthalide (BP).

Depending on the need, age, body weight, and health conditions of the subject, the medicament provided in accordance with the present invention could be dosed at various administration frequencies, such as once a day, multiple times a day, or once every few days, etc. For example, when the medicament provided in accordance with the present invention is administered by oral administration to a subject to inhibit the accumulation of white fat, promote the conversion of white fat into brown fat, inhibit weight gain and/or reduce the contents of triglycerides, glucose, total cholesterol in blood, the medicament is administered at an amount ranging from about 30 mg (as BP)/kg-body weight to about 2000 mg (as BP)/kg-body weight per day, preferably ranging from about 100 mg (as BP)/kg-body weight to about 1,000 mg (as BP)/kg-body weight per day, and more preferably ranging from about 200 mg (as BP)/kg-body weight to about 500 mg (as BP)/kg-body weight per day, wherein the unit "mg/kg-body weight" refers to the amount required for per kg-body weight of the subject. In some embodiments of the present invention, the medicament provided in accordance with the present invention is used for anti-obesity (i.e., inhibiting the accumulation of white fat, promoting the conversion of white fat into brown fat, inhibiting weight gain and/or reducing the contents of triglycerides, glucose and total cholesterol in blood), wherein the medicament is administered at an amount of about 250 mg (as BP)/kg-body weight per day.

Besides the administration of the medicament provided in accordance with the present invention, additional mesenchymal stem cells and/or brown-like adipose cells could be optionally administered to the subject in need, and the mesenchymal stem cells and/or brown-like adipose cells could be administered in combination with the medicament simultaneously or separately. Depending on the need, age, body weight and health conditions of the subject, the mesenchymal stem cells and/or brown-like adipose cells could be administered at various frequencies, such as once a day, multiple times a day, once every few days, or once every few weeks, etc. For example, when the cells are administered to the subject by cell infusion, the cells are administered at an amount ranging from about $4\times10^4$ cells to about $4\times10^6$ cells every two weeks, based on the total amount of mesenchymal stem cells and brown-like adipose cells. In some embodiments of the present invention, besides administering the medicament provided in accordance with the present invention to a subject in need, the subject could further be administered with about $4\times10^5$ adipose stem cells or about $4\times10^5$ brown-like adipose cells by cell infusion every two weeks.

The present invention also relates to a method for inhibiting the accumulation of white fat, promoting the conversion of white fat into brown fat, inhibiting weight gain and/or reducing the contents of triglycerides, glucose and total cholesterol in blood, comprising administering to a subject in need an effective amount of butylidenephthalide (BP). The method is especially for anti-obesity and/or preventing metabolic syndrome associated with obesity. The applied route, applied type, applied amount, applied form in combination and uses in related applications of butylidenephthalide (BP) are all in line with the above descriptions.

The present invention will be further illustrated in detail with specific examples as follows. However, the following examples are provided only for illustrating the present invention. The scope of the present invention is not limited thereby and will be indicated in the appended claims.

EXAMPLES

[Cellular Experiment]

A1. Preparation of a Conditional Medium

A DMEM medium (brand name: GIBCO; product number: 11965092) was used as a basic medium, and rosiglitazone (concentration: 0.5 µM, solvent: dimethyl sulfoxide (DMSO)), insulin (concentration: 170 nM, solvent: culture medium), 3-isobutyl-1-methylxanthine (IBMX; concentration: 0.5 µM, solvent: DMSO) and dexamethasone (concentration: 1 µM, solvent: DMSO) were externally added therein to provide a conditional medium.

B1. Cell Cultivation

B1-1. Pre-Cultivation of Adipose Stem Cells

The adipose stem cells (ADSCs) were cultivated in a DMEM/F12 medium at 37° C., 5% $CO_2$ for 5 days. The morphology of aforementioned pre-cultivated cells was observed at different magnifications (including 40-fold, 100-fold and 200-fold) by a microscope and taken photos. The results are shown in FIG. 1 (i.e., adipose stem cells (undifferentiated)).

B1-2. Differentiation of Adipose Stem Cells

The aforementioned pre-cultivated adipose stem cells provided by Example B1-1 were cultivated in a conditional medium provided by Example A1 at 37° C., 5% $CO_2$ for 7 days to differentiate into adipose cells. The morphology of the cells thus obtained was observed at different magnifications (including 40-fold, 100-fold and 200-fold) by a microscope and taken photos. The results are also shown in FIG. 1 (i.e., adipose cells (differentiated)).

B1-3. Conversion of Adipose Cells

The adipose cells provided by Example B1-2 were divided into seven groups and independently subjected to the following treatments:

(1) Control group: cells were cultivated in a conditional medium provided by A1 for 7 days;

(2) BP-2 group: cells were cultivated in a conditional medium that was externally added with butylidenephthalide (BP) (to a final concentration of 2 µg/mL) for 7 days (butylidenephthalide (BP) was purchased from ECHO CHEMICAL Co., Ltd. (Taiwan); product number: A10353);

(3) BP-10 group: cells were cultivated in a conditional medium that was externally added with butylidenephthalide (BP) (to a final concentration of 10 µg/mL) for 7 days;

(4) BP-50 group: cells were cultivated in a conditional medium that was externally added with butylidenephthalide (BP) (to a final concentration of 50 µg/mL) for 7 days;

(5) Tofacitinib group: cells were cultivated in a conditional medium that was externally added with tofacitinib (to a final concentration of 2 µM) for 7 days (tofacitinib was purchased from UNI-ONWARD Corp. (Taiwan); product number: PZ0017);

(6) Adenosine group: cells were cultivated in a conditional medium that was externally added with adenosine (to a final concentration of 1 µM) for 7 days (adenosine was purchased from UNI-ONWARD Corp. (Taiwan); product number: A4036); and (7) Proanthocyanidin group: cells were cultivated in a conditional medium that was externally added with proanthocyanidin (to a final concentration of 10 µM) for 7 days (adenosine was purchased from Hong Jing Co., Ltd. (Taiwan); product number: sc-344976).

Then, the morphology of cells in each group was observed at different magnifications (including 40-fold, 100-fold and 200-fold) by a microscope and taken photos. The results of "BP-10 group" are also shown in FIG. 1.

Example 1: Effect of Butylidenephthalide (BP) on Promoting the Differentiation of a Stem Cell into a Brown-Like Adipose Cell As described above, different from white adipose cells, the morphology of brown-like adipose cells/brown adipose cells is characterized by (i) containing numerous adipose droplets, (ii) containing a large number of mitochondria and (iii) having highly expressed uncoupling protein 1 (UCP1). Because of containing a large number of mitochondria, brown-like adipose cells/brown adipose cells possess higher oxygen consumption rate and spare respiratory capacity (wherein the spare respiratory capacity refers to the difference between the maximum oxygen consumption rate and the basic oxygen consumption rate, representing the oxygen consumption that is not used for producing ATP), as compared to white adipose cells. Therefore, the number and proportion of brown-like adipose cells/brown adipose cells can be conceived by observing the number of adipose droplets in the cells, the oxygen consumption rate of adipose cells and the gene and protein expressions of UCP1.

(1-1) Observation of the Production Efficiency of Adipose Droplets in Cells

First, the cell morphology of each group in photos taken in Examples B1-1, B1-2 and B1-3 was observed. As shown in FIG. 1, as compared to the adipose stem cells (undifferentiated) provided by Example B1-1 and adipose cells (differentiated) provided by Example B1-2, the adipose cells in "BP-10 group" provided by Example B1-3 contained more adipose droplets. The results indicate that the use of BP can effectively promote the differentiation of an adipose stem cell into a brown-like adipose cell.

Figure 2A:
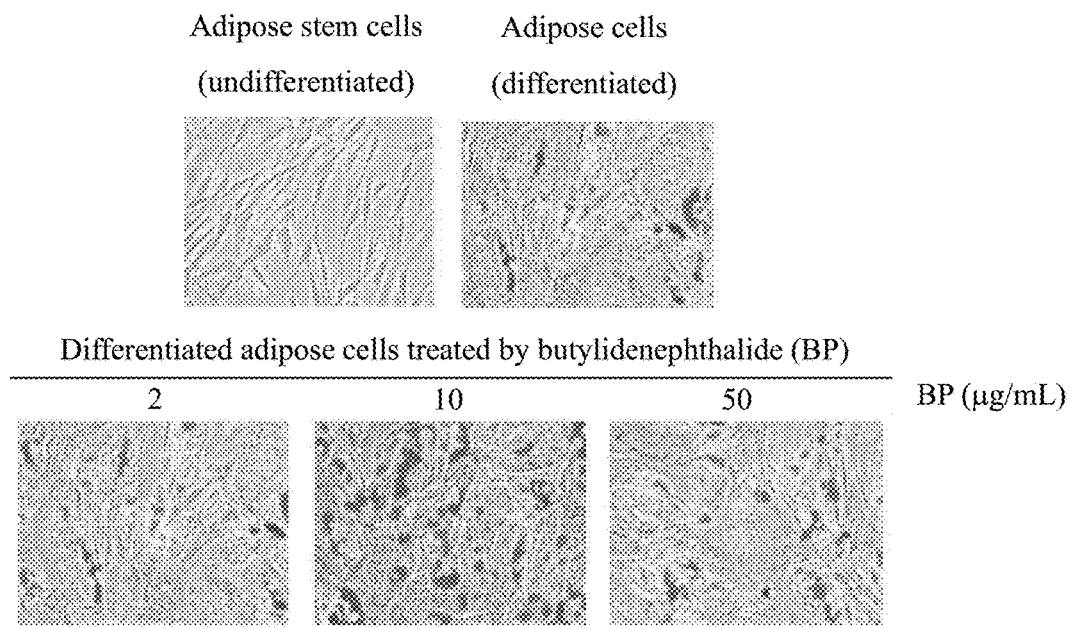
Figure 2B:
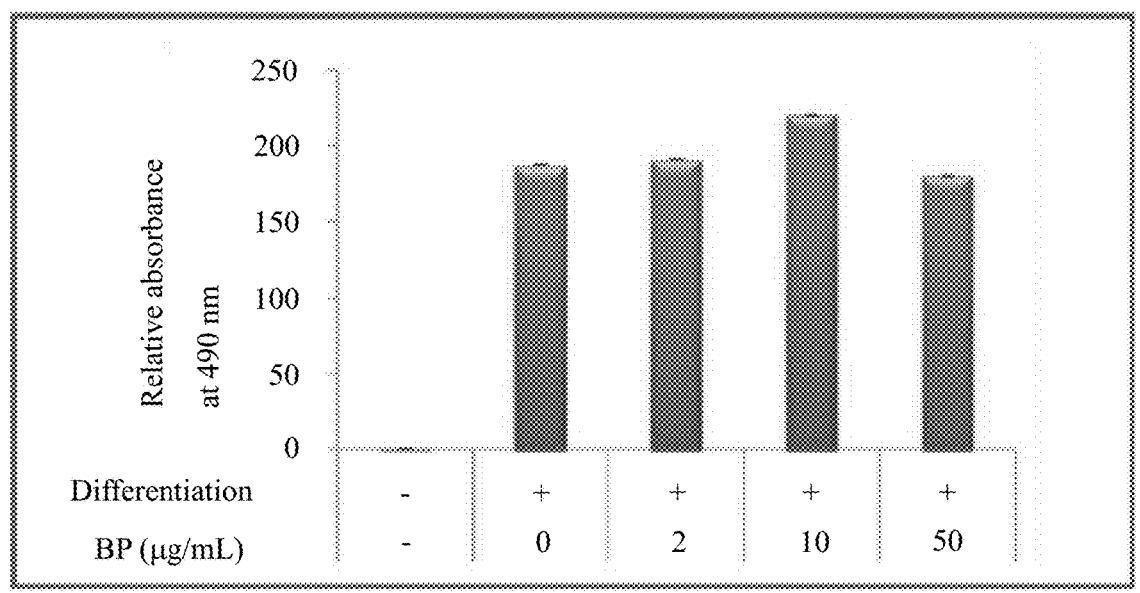

Thereafter, the adipose droplets of adipose stem cells (undifferentiated) provided by Example B1-1, adipose cells (differentiated) provided by Example B1-2 and adipose cells in "BP-2 group", "BP-10 group" and "BP-50 group" provided by Example B1-3 were stained by oil red dye, and the morphology thereof was taken photos and recorded. The results are shown in FIG. 2A. Then, the number of adipose droplets of adipose cells in each group was quantified. The results are shown in FIG. 2B. As shown in FIGS. 2A and 2B, as compared to the adipose cells that were not treated by butylidenephthalide (BP), the adipose cells that were treated by butylidenephthalide (BP) in "BP-2 group", "BP-10 group" and "BP-50 group" contained more adipose droplets, wherein the adipose cells in "BP-10 group" had the highest content of adipose droplets. The results indicate that the use of BP can effectively promote the differentiation of an adipose stem cell into a brown-like adipose cell.

(1-2) Observation of the Efficiency of Enhancing Oxygen Consumption Rate

The adipose stem cells (undifferentiated) provided by Example B1-1, adipose cells (differentiated) provided by Example B1-2 and adipose cells in "BP-2 group", "BP-10 group" and "BP-50 group" provided by Example B1-3 were separately seeded in a XF 24-well cell culture plate (purchased from Seahorse Bioscience) with a density of $1.65 \times 10^4$ cells/well and cultivated in a DMEM medium free of buffer ingredients (i.e., the medium containing 2 mM GlutaMAX, 1 mM sodium pyruvate, 1.85 g/L NaCl, 25 mM glucose) at 37° C. for 24 hours. After a medium was replaced with a fresh medium, the cells were continuously cultivated at 37° C. for 1 hour. Then, the mitochondrial biosynthesis of cells in each group was separately interfered with 25 µM oligomycin, 0.5 µM FCCP and 5 µM rotenone/antimycin A sequentially, and was continuously detected by a XF24 extracellular flux analyser (purchased from Seahorse Bioscience) prior to and during conduction of the aforementioned interference. The oxygen tension and acidification degree in the culture medium were detected by an adjusted probe to further calculate the oxygen consumption rate and spare respiratory capacity. The results of oxygen consumption rate are shown in FIG. 3A, and the results of basic oxygen consumption rate and spare respiratory capacity are shown in FIG. 3B.

Figure 3A:
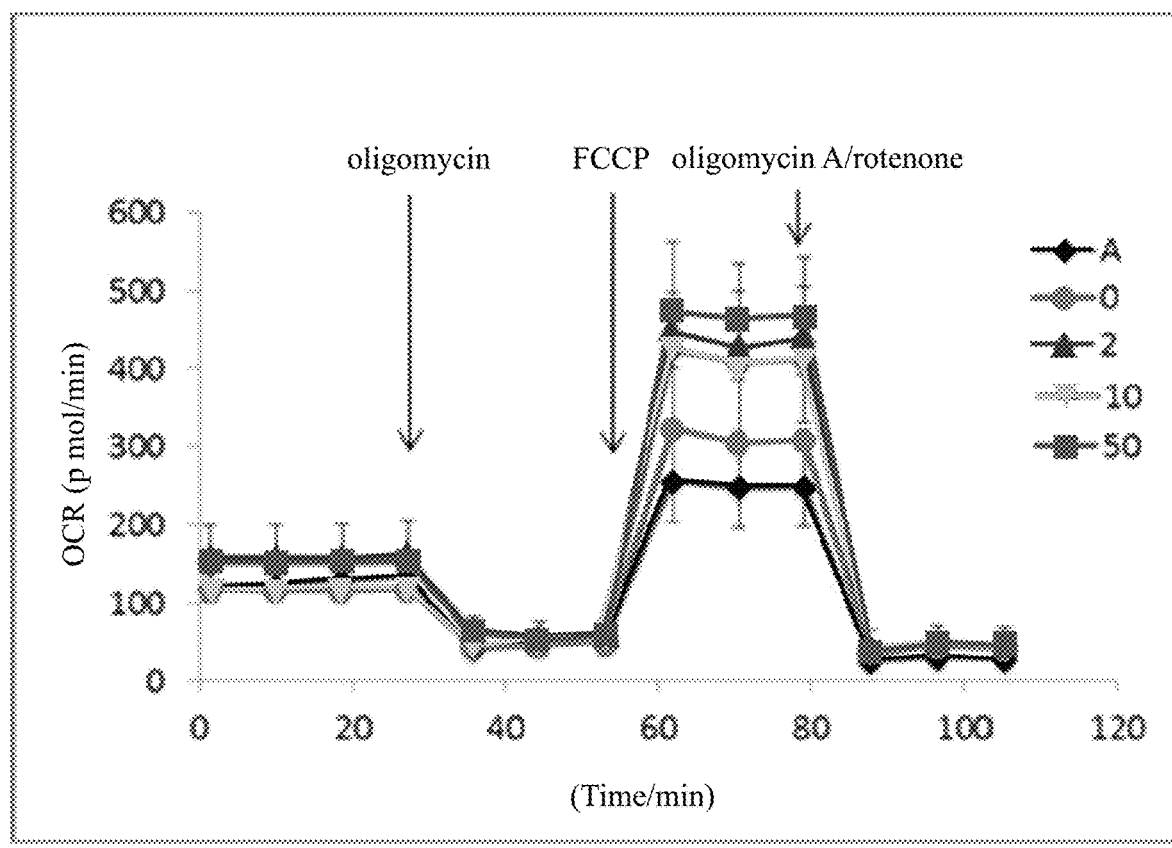
Figure 3B:
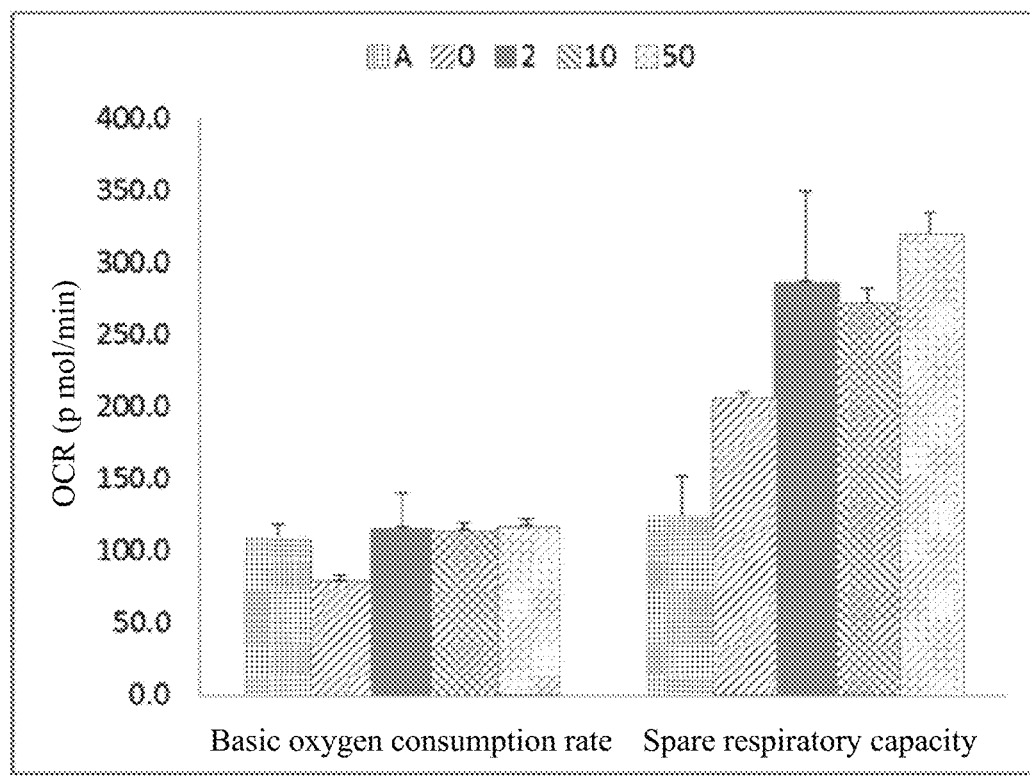

As shown in FIGS. 3A and 3B, as compared to the adipose cells (differentiated) that were not treated by butylidenephthalide (BP), the cells that were treated by butylidenephthalide (BP) in "BP-2 group", "BP-10 group" and "BP-50 group" had higher oxygen consumption rate (FIG. 3A) and spare respiratory capacity (FIG. 3B). The results indicate that the use of BP can effectively promote the differentiation of an adipose stem cell into a brown-like adipose cell.

(1-3) Analysis of UCP1 Expression

The cells in each group provided by Example B1-3 were separately collected, and then the total RNA and protein of the cells were individually extracted for the following experimentation.

Figure 4A:
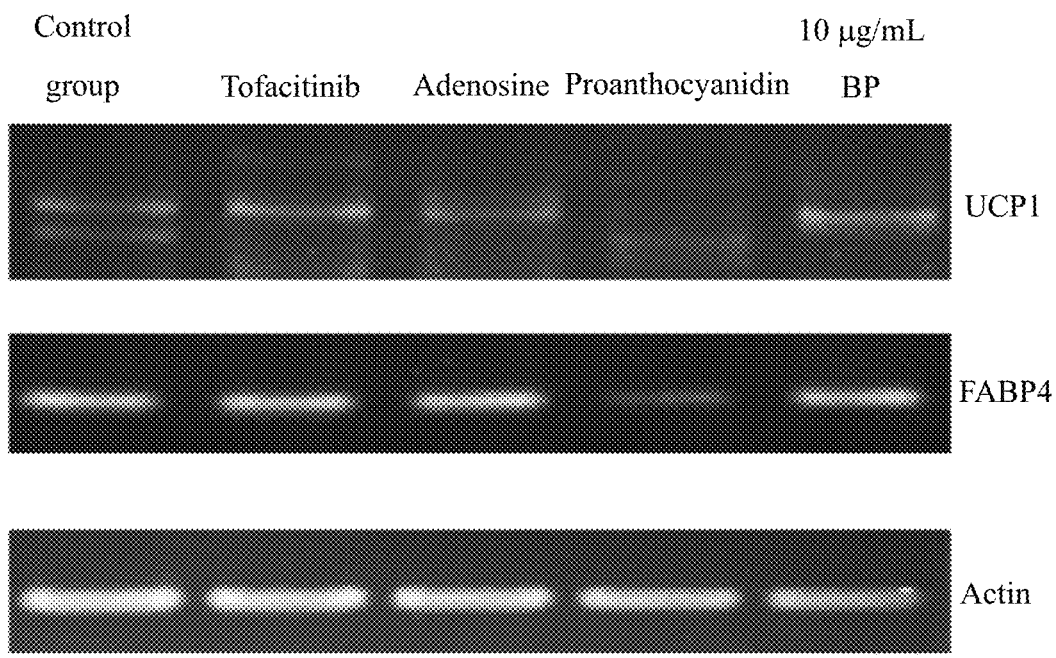
Figure 4B:
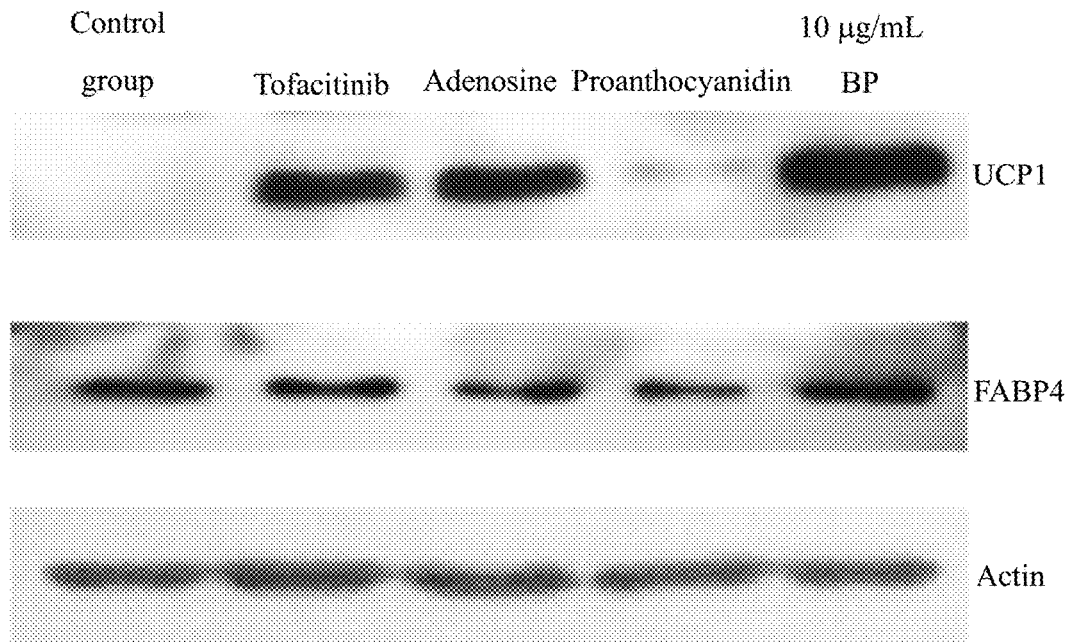

The total RNA was subjected to reverse transcription to provide cDNA, and then the expression of UCP1 gene of the cells in each group was analyzed by reverse transcription polymerase chain reaction (RT-PCR). The results are shown in FIG. 4A, wherein FABP4 gene was a biomarker of mature adipose cells, and thus, it was used as an internal control of adipose cells in this experimentation. The actin gene was used as an internal control of all the cells. Furthermore, the expression of UCP1 protein of the cells in each group was analyzed by Western blot. The results are shown in FIG. 4B, wherein FABP4 protein was used as an internal control of adipose cells. The actin was used as an internal control of all the cells.

As shown in FIGS. 4A and 4B, as compared to that of control group, the expressions of UCP1 gene and UCP1 protein of "BP-10 group" both significantly increased, and the increments of UCP1 gene and UCP1 protein were higher than that of tofacitinib group, adenosine group and proanthocyanidin group. The results indicate that the use of BP can effectively promote the differentiation of an adipose stem cell into a brown-like adipose cell.

As shown by the results of aforementioned Examples (1-1) to (1-3), BP can effectively promote the differentiation of a stem cell into a brown-like adipose cell, and the effect is better than that of the known drugs capable of promoting the differentiation of a stem cell into a brown-like adipose cell, including tofacitinib, adenosine and proanthocyanidin.

[Animal Experiment]

A2. Preparation of Experimental Animal Mouse Model

The C57BL/6 mice (purchased from National Laboratory Animal Center, Taiwan) were bred in Laboratory Animal Center of China Medical University, Taiwan (conditions: 3 mice were bred per cage; the temperature of the breeding room ranged from 20° C. to 24° C., and the relative humidity ranged from 50% to 70%; the light cycle was 12 hours; sufficient water and normal diet were supplied daily) until they were 4 weeks old. Then, the mice were randomly divided into seven groups (six mice per group), and individually subjected to the following treatment and experimentation:

(1) Normal diet group (i.e., "ND" group): the mice were continuously fed with a normal diet until they were 18 weeks old.

(2) High fat diet group (i.e., "HFD" group): the mice were continuously fed with a high fat diet until they were 18 weeks old, and no additional treatment was conducted.

(3) Oral administration of butylidenephthalide (BP) group (i.e., "HFD+BP" group): the mice were continuously fed with a high fat diet, and then simultaneously administered with butylidenephthalide (BP) by oral route at the beginning of the ninth week (dosage amount: every day, 250 mg/kg-body weight) until they were 18 weeks old.

(4) Cell infusion of adipose stem cells group (i.e., "HFD+ADSC" group): the mice were continuously fed with a high fat diet, and then simultaneously administered with adipose stem cells by intravenous injection at the beginning of the eleventh week (dosage amount: every two weeks, $4\times10^5$ cells suspended in 100~150 μL of normal saline) until they were 18 weeks old (four injections in total).

(5) Oral administration of butylidenephthalide (BP) in combination with cell infusion of adipose stem cells group (i.e., "HFD+BP+ADSC" group): the mice were continuously fed with a high fat diet, then simultaneously administered with butylidenephthalide (BP) by oral route at the beginning of the ninth week (dosage amount: every day, 250 mg/kg-body weight), and further simultaneously administered with adipose stem cells by intravenous injection at the beginning of the eleventh week (dosage amount: every two weeks, $4\times10^5$ cells suspended in 100~150 μL of normal saline) until they were 18 weeks old (four injections in total).

(6) Cell infusion of brown-like adipose cells group (i.e., "HFD+BLC" group): the mice were fed with a high fat diet, and then simultaneously administered with brown-like adipose cells provided by Example 1 by intravenous injection at the beginning of the eleventh week (dosage amount: every two weeks, $4\times10^5$ cells suspended in 100~150 μL of normal saline) until they were 18 weeks old (four injections in total).

(7) Oral administration of butylidenephthalide (BP) in combination with cell infusion of brown-like adipose cells group (i.e., "HFD+BP+BLC" group): the mice were continuously fed with a high fat diet, then simultaneously administered with butylidenephthalide (BP) by oral route (dosage amount: every day, 250 mg/kg-body weight) at the beginning of the ninth week, and further simultaneously administered with brown-like adipose cells provided by Example 1 by intravenous injection at the beginning of the eleventh week (dosage amount: every two weeks, $4\times10^5$ cells suspended in 100~150 μL of normal saline) until they were 18 weeks old (four injections in total).

The standard diet (1326, Altromin, Lage, Germany; purchasing broker: ejoy2 Co., Ltd.) is a granulated diet with the granule size of 13 mm, containing 19% of crude protein, 4% of crude fat, 6% of crude fiber, 13.5% of water, 7% of gray matter and 50.5% of non-nitrogen compound therein. The high fat diet (TD.06415, Harlan, Frederick, State of Maryland, U.S.A; purchasing broker:ejoy2 Co., Ltd.) is a special formulated diet mixing with lard and soybean oil, containing 22.7% of fat (as weight) and 22.8% of sucrose (as weight) therein, and the amount of heat is 4.6 kcal/g, wherein 45% of calories are from fat.

B2. Observation, Recordation and Sample Collection of Mouse Model

B2-1. In the preparation process of above Example A2, the weight change of mice was recorded every week until they were 18 weeks old.

B2-2. After Example B2-1 was accomplished, the mice was subjected to fast for 12 hours, and then the blood of mice was collected in a serum tube by cardic blood collection. The collected blood was stand for 30 minutes, and then subjected to centrifuge at 3000 rpm, 4° C. for 10 minutes. The supernatant thus provided was collected (i.e., blood sample) and kept at a temperature of 4° C. for following experimentation and analysis.

B2-3. After Example B2-2 was accomplished, the mice were sacrificed, and the liver, heart, kidney, subcutaneous adipose tissue and visceral adipose tissue thereof were taken out to take photos. The weight of the subcutaneous adipose tissue and visceral adipose tissue of mice were measured and recorded, and the collected organs were kept at a temperature of −80° C. for following experimentation and analysis.

Example 2: Observation of the Condition of Mouse Fat Browning

It is known that there are numerous small adipose droplets in brown adipose cells. To understand whether butylidenephthalide (BP) is effective in promoting the occurrence of the fat browning in an animal body or not, the subcutaneous adipose tissue and visceral adipose tissue provided by Example B2-3 were fixed by formalin, mounted by wax, and then sliced. The aforementioned slices were stained by hematoxylin-eosin stain (H&E stain) to observe the cell morphology of adipose tissue of mice in each group. The results are shown in FIG. 5A (subcutaneous fat) and 5B (visceral fat).

Figure 5A:
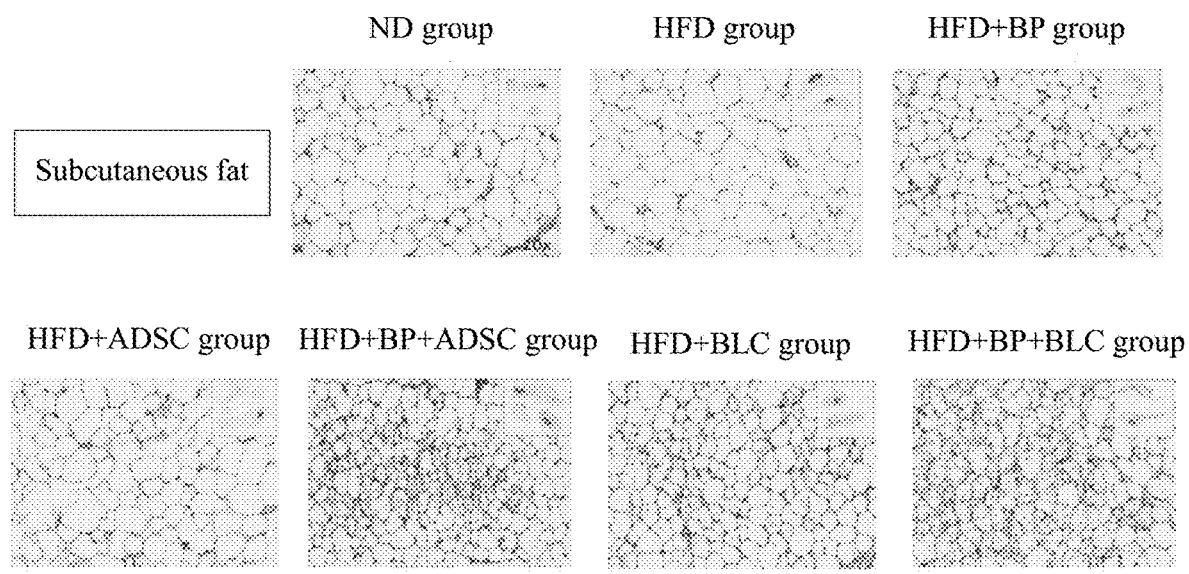
Figure 5B:
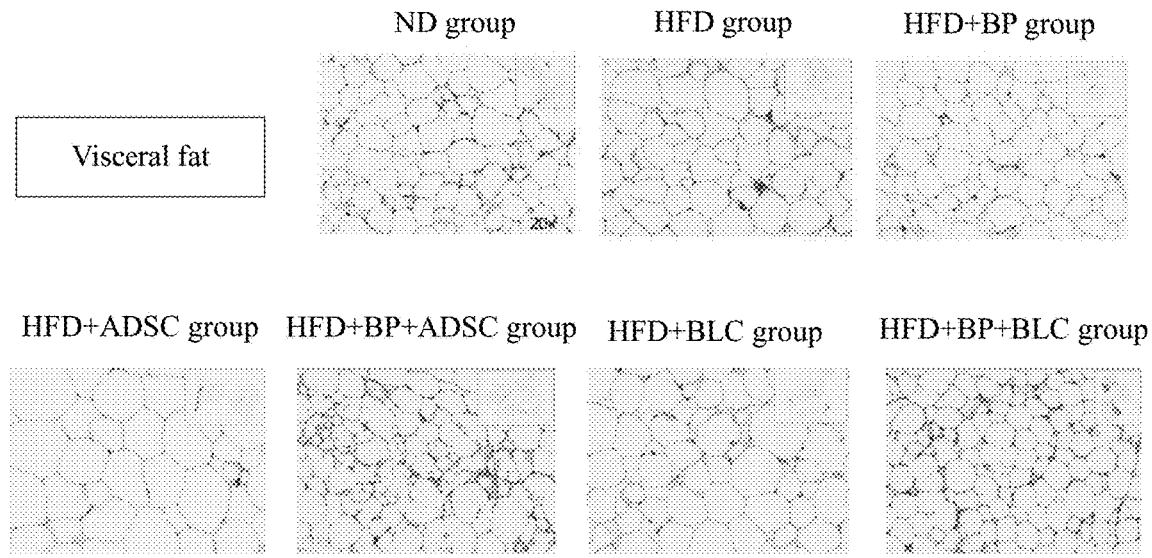

As shown in FIGS. 5A and 5B, the subcutaneous adipose tissue and visceral adipose tissue of mice in "HFD" group both consist of single and large white adipose cells, and those in "HFD+BP" group, "HFD+ADSC" group, "HFD+BP+ADSC" group, "HFD+BLC" group and "HFD+BP+BLC" group contained the brown adipose cells with numerous small adipose droplets. In addition, as compared to the "HFD+BP" group or "HFD+ADSC" group, mice in "HFD+BP+ADSC" group had significantly larger number of brown adipose cells with numerous small adipose droplets. On the other hand, as compared to the "HFD+BP" group or "HFD+BLC" group, mice in "HFD+BP+BLC" group had significantly larger number of brown adipose cells with numerous small adipose droplets.

The results indicate that the administration of butylidenephthalide (BP) alone and the administration of butylidenephthalide (BP) in combination with cell infusion can both effectively convert the white fat of mice induced by a high fat diet into brown adipose cells with numerous small adipose droplets. That is, butylidenephthalide (BP) and a combination of BP and cell infusion both are effective in promoting the fat browning in an animal body, wherein the effect of a combination of BP and cell infusion is better.

Figure 6A:
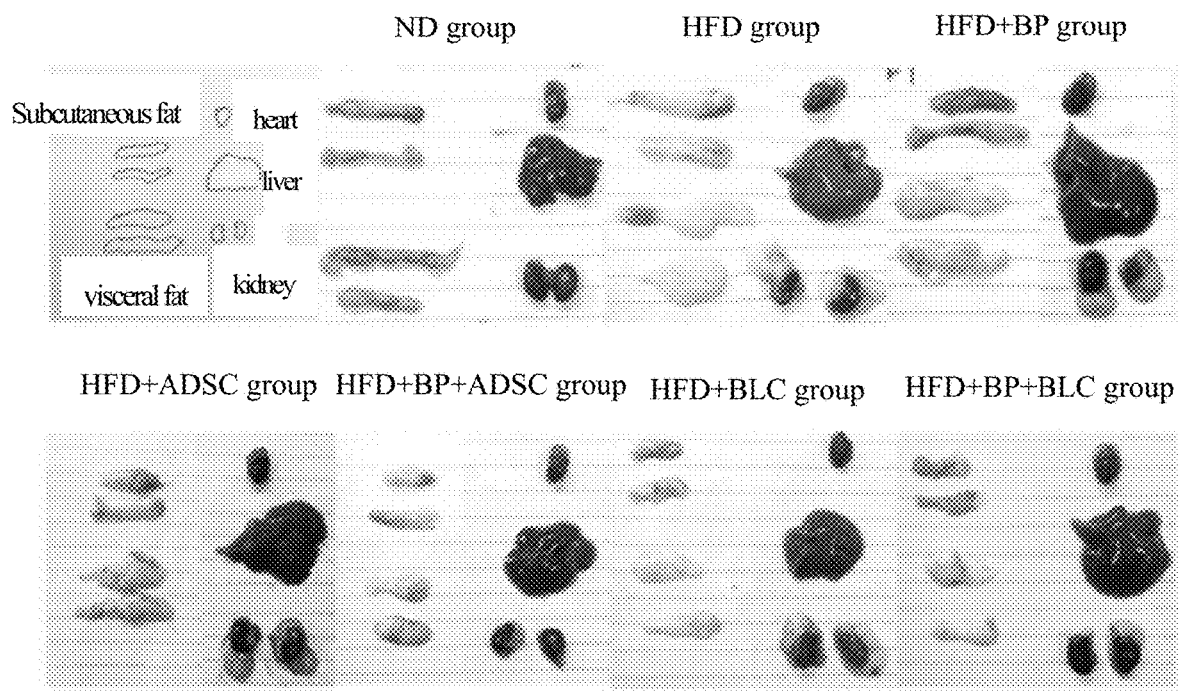

Example 3: Appearances of the Heart, Liver, Kidney, Subcutaneous Adipose Tissue and Visceral Adipose Tissue of Mice To understand whether butylidenephthalide (BP) can alleviate the accumulation of white fat or not, the photos of appearances of the liver, heart, kidney, subcutaneous adipose tissue and visceral adipose tissue of mice in each group recorded in Example B2-3 are shown in FIG. 6A. The weight of subcutaneous adipose tissue and visceral adipose tissue of mice in each group recorded in Example B2-3 were respectively averaged. The results are shown in Table 1, FIGS. 6B and 6C.

TABLE 1

|  | Subcutaneous adipose tissue (g) | Visceral adipose tissue (g) |
| --- | --- | --- |
| "ND" group | 0.22 | 0.59 |
| "HFD" group | 0.42 | 1.0 |
| "HFD + BP" group | 0.24 | 0.57 |
| "HFD + ADSC" group | 0.31 | 0.62 |
| "HFD + BP + ADSC" group | 0.28 | 0.64 |

TABLE 1-continued

|  | Subcutaneous adipose tissue (g) | Visceral adipose tissue (g) |
| --- | --- | --- |
| "HFD + BLC" group | 0.21 | 0.54 |
| "HFD + BP + BLC" group | 0.20 | 0.46 |

As shown in FIG. 6A, as compared to that of "ND" group, the visceral of mice in "HFD" group contained a large amount of accumulated white fat, wherein the accumulation condition surrounding kidney was most serious. However, as compared to that of "HFD" group, the accumulation condition of white fat in visceral of mice in "HFD+BP" group, "HFD+ADSC" group, "HFD+BP+ADSC" group, "HFD+BLC" group and "HFD+BP+BLC" group significantly alleviated. On the other hand, as compared to that of "HFD+BP" group or "HFD+ADSC" group, the condition of mice in "HFD+BP+ADSC" group was alleviated more significantly. In addition, as compared to that of "HFD+BP" group or "HFD+BLC" group, the condition of mice in "HFD+BP+BLC" group was alleviated more significantly.

Figure 6B:
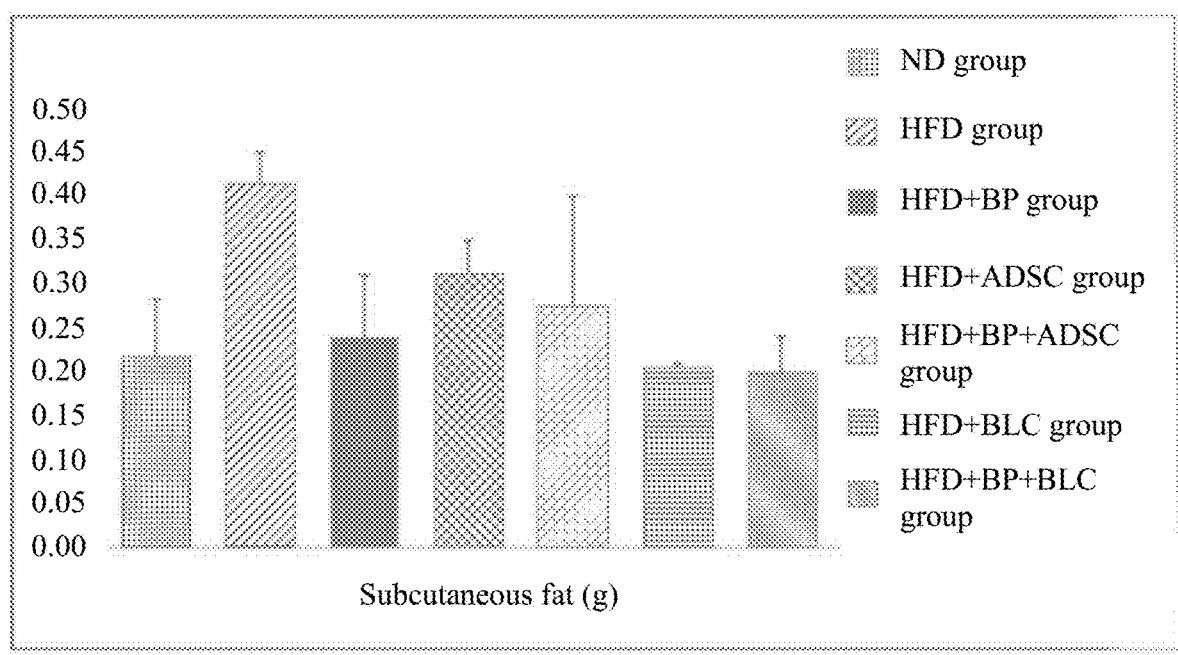
Figure 6C:
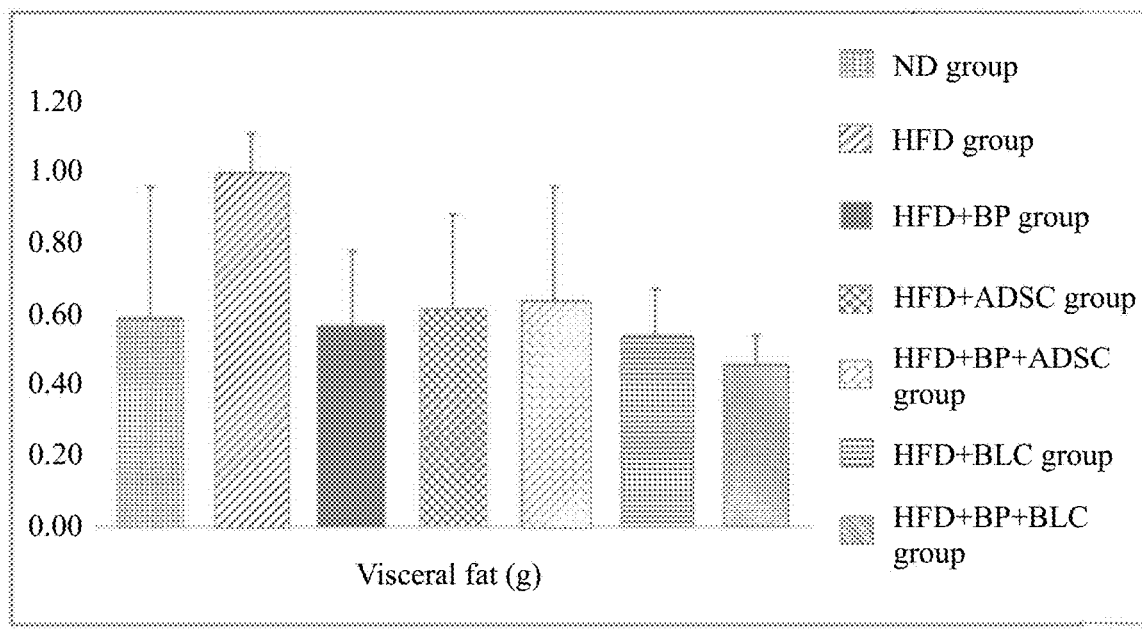

As shown in Table 1, FIGS. 6B and 6C, as compared to that of "ND" group, the weights of subcutaneous fat and visceral fat in "HFD" group were both significantly higher. However, as compared to that of "HFD" group, the weights of subcutaneous fat and visceral fat in "HFD+BP" group, "HFD+ADSC" group, "HFD+BP+ADSC" group, "HFD+BLC" group and "HFD+BP+BLC" group were all significantly lower.

The results indicate that the administration of butylidenephthalide (BP) alone and the administration of butylidenephthalide (BP) in combination with cell infusion can both effectively reduce the accumulation of subcutaneous white fat and visceral white fat of mice induced by a high fat diet, wherein the effect of a combination of butylidenephthalide (BP) and cell infusion is better.

Figure 7:
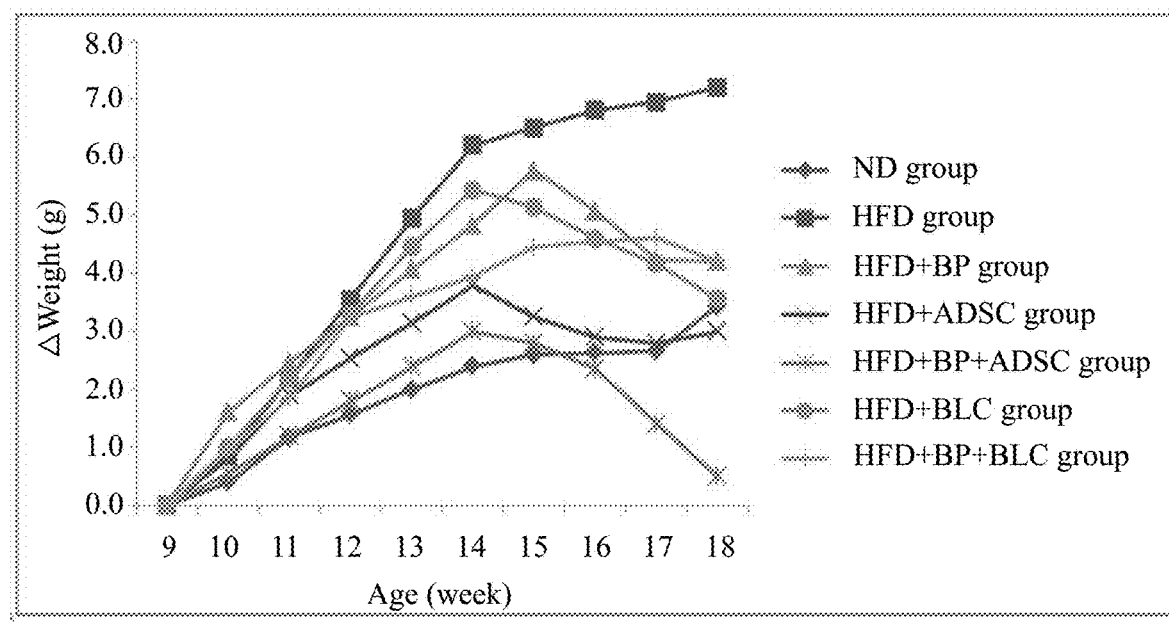
FIG. 7 is a curve diagram showing the effect of butylidenephthalide (BP) and cell infusion on mouse weight by showing the change of mouse weight during 9 weeks to 18 weeks old, including the results of "ND group", "HFD group", "HFD+BP group", "HFD+ADSC group", "HFD+BP+ADSC group", "HFD+BLC group" and "HFD+BP+BLC group"

Example 4: Observation of the Changes of Mouse Physiological Parameters 4-1. Changes of Mouse Weight To understand whether butylidenephthalide (BP) is effective in inhibiting weight gain or not, the average value of the recorded weights of mice in each group of Example B2-1 was obtained weekly. The results are shown in FIG. 7. As shown in FIG. 7, as compared to that of "HFD" group, the weights of mice in "HFD+BP" group, "HFD+ADSC" group, "HFD+BP+ADSC" group, "HFD+BLC" group and "HFD+BP+BLC" group increased significantly less. On the other hand, as compared to that of "HFD+BP" group or "HFD+ADSC" group, the weights of mice in "HFD+BP+ADSC" group increased significantly less. In addition, as compared to that of "HFD+BP" group or "HFD+BLC" group, the weights of mice in "HFD+BP+BLC" group increased significantly less.

The results indicate that the administration of butylidenephthalide (BP) alone and the administration of butylidenephthalide (BP) in combination with cell infusion can both effectively inhibit weight gain of mice induced by a high fat diet, wherein the effect of a combination of butylidenephthalide (BP) and cell infusion on inhibiting weight gain is better.

4-2. Contents of Glucose, Triglycerides and Total Cholesterol in Blood

To understand whether butylidenephthalide (BP) is effective in reducing the contents of glucose, triglycerides and total cholesterol in blood or not, the blood sample of mice in each group provided by Example B2-2 was detected by a SYSMEX K-1000 and TOSHIBA TBA200FA automatic blood analyzer to analyze the contents of glucose, triglycerides and total cholesterol in blood of mice. The results of each group were averaged. The results are shown in Table 2 and FIGS. 8A to 8C. Based on the result of "HFD" group, the relative contents of glucose, triglycerides and total cholesterol of each group were calculated. The results are also shown in Table 2.

total cholesterol in blood of mice induced by a high fat diet, wherein the effect of a combination of butylidenephthalide (BP) and cell infusion is better.

As shown by the above results of cellular and animal experiments, butylidenephthalide (BP) is capable of promoting the differentiation of a stem cell into a brown-like adipose cell, inhibiting the accumulation of white fat, promoting the conversion of white fat into brown fat, inhibiting weight gain and/or reducing the contents of triglycerides,

TABLE 2

Serum biochemical values of mice in groups fed by a normal diet or a high fat diet

|  | ND | HFD | HFD + BP | HFD + ADSC | HFD + BP + ADSC | HFD + BLC | HFD + BP + BLC |
|---|---|---|---|---|---|---|---|
| Glucose (mg/dL) | 229.67 ± 27.48 | 484.50 ± 70.50 | 411.50 ± 43.50 | 362.50 ± 46.50 | 333.00 ± 41.00 | 327.00 ± 91.00 | 291.50 ± 77.50 |
| Relative content of glucose | — | 100 | 85 | 75 | 69 | 67 | 60 |
| Triglycerides (mg/dL) | 149.00 ± 8.16 | 253.00 ± 33.00 | 213.50 ± 50.50 | 234.50 ± 24.50 | 157.00 ± 14.00 | 109.50 ± 44.50 | 219.50 ± 15.50 |
| Relative content of triglycerides | — | 100 | 84 | 93 | 62 | 43 | 87 |
| Total cholesterol (mg/dL) | 55.00 ± 0.00 | 197.00 ± 34.00 | 157.50 ± 1.50 | 105.50 ± 4.50 | 123.00 ± 14.00 | 165.00 ± 35.00 | 149.50 ± 39.50 |
| Relative content of total cholesterol | — | 100 | 80 | 54 | 62 | 84 | 76 |

Figure 8A:
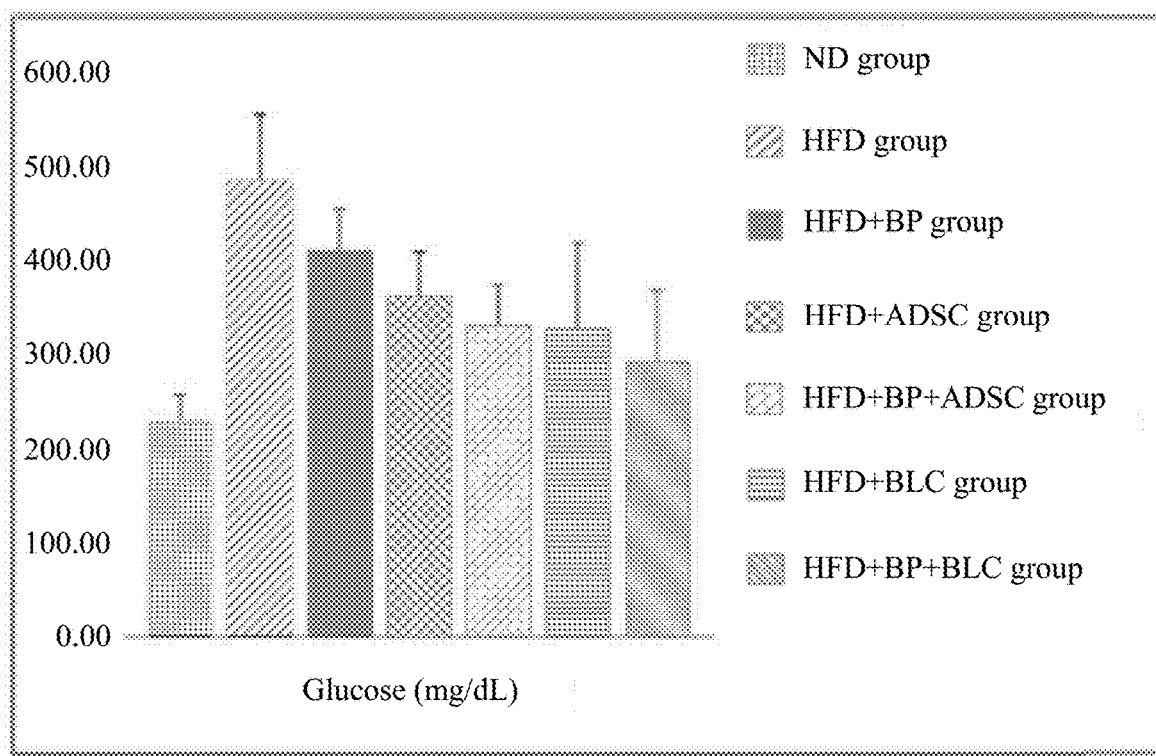

As shown in Table 2 and FIG. 8A, as compared to that of "ND" group, the content of glucose in blood of mice in "HFD" group was significantly higher. However, as compared to that of "HFD" group, the contents of glucose in blood of mice in "HFD+BP" group, "HFD+ADSC" group, "HFD+BP+ADSC" group, "HFD+BLC" group and "HFD+BP+BLC" group were all significantly lower. On the other hand, as compared to that of "HFD+BP" group or "HFD+ADSC" group, the content of glucose in blood of mice in "HFD+BP+ADSC" group was lower. In addition, as compared to that of "HFD+BP" group or "HFD+BLC" group, the content of glucose in blood of mice in "HFD+BP+BLC" group was lower.

Figure 8B:
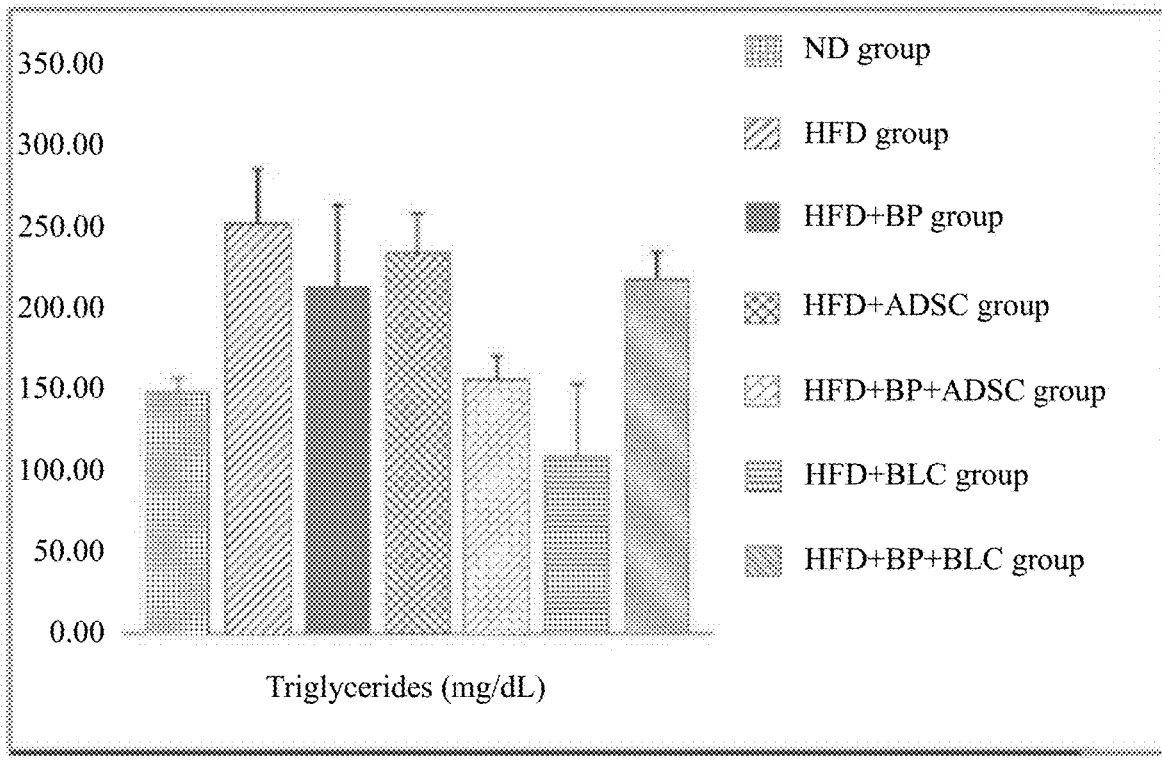

As shown in Table 2 and FIG. 8B, as compared to that of "ND" group, the content of triglycerides in blood of mice in "HFD" group was significantly higher. However, as compared to that of "HFD" group, the contents of triglycerides in blood of mice in "HFD+BP" group, "HFD+ADSC" group, "HFD+BP+ADSC" group, "HFD+BLC" group and "HFD+BP+BLC" group were all significantly lower. On the other hand, as compared to that of "HFD+BP" group or "HFD+ADSC" group, the content of triglycerides in blood of mice in "HFD+BP+ADSC" group was lower.

Figure 8C:
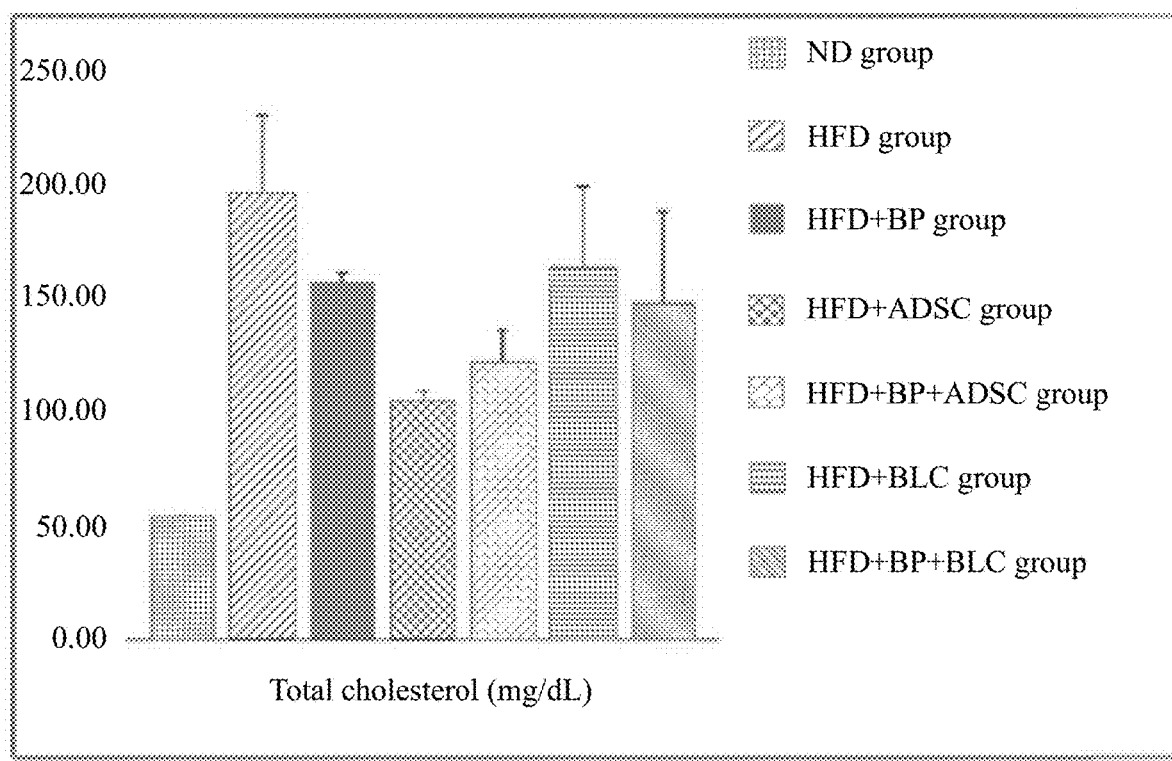

As shown in Table 2 and FIG. 8C, as compared to that of "ND" group, the content of total cholesterol in blood of mice in "HFD" group was significantly higher. However, as compared to that of "HFD" group, the contents of triglycerides in blood of mice in "HFD+BP" group, "HFD+ADSC" group, "HFD+BP+ADSC" group, "HFD+BLC" group and "HFD+BP+BLC" group were all significantly lower. On the other hand, as compared to that of "HFD+BP" group, the content of triglycerides in blood of mice in "HFD+BP+ADSC" group was lower. In addition, as compared to that of "HFD+BP" group or "HFD+BLC" group, the content of triglycerides in blood of mice in "HFD+BP+BLC" group was lower.

The results indicate that the administration of butylidenephthalide (BP) alone and the administration of butylidenephthalide (BP) in combination with cell infusion can both effectively reduce the contents of glucose, triglycerides and total cholesterol in blood, and thus, can be administered to an animal to anti-obesity and/or prevent metabolic syndrome associated with obesity. Particularly, the metabolic syndrome associated with obesity is at least one of diabetes mellitus, cerebrovascular disease, cardiovascular disease, hypertension and nephropathy. In addition, administration of butylidenephthalide (BP) with mesenchymal stem cells and/or brown-like adipose cells can further enhance the aforementioned effects.

The above embodiments are only used to illustrate the principle and function of the present invention, and the scope of the present invention is not limited thereby. Without departing from the principle and spirit of the present invention, people skilled in the art can modify and change the above embodiments. The scope of the present invention is indicated in the appended claims

What is claimed is:

1. A method for inhibiting the accumulation of white fat, promoting the conversion of white fat into brown fat, inhibiting weight gain and/or reducing the contents of triglycerides, glucose and total cholesterol in blood, comprising administering to a subject in need an effective amount of butylidenephthalide (BP), and the butylidenephthalide (BP) is administered with at least one from the group consisting of a mesenchymal stem cell and a brown-like adipose cell.

2. The method as claimed in claim 1, wherein the method prevents obesity and/or metabolic syndrome associated with obesity.

3. The method as claimed in claim 2, wherein the metabolic syndrome is at least one of diabetes mellitus, cerebrovascular disease, cardiovascular disease, hypertension and nephropathy.

4. The method as claimed in claim 3, wherein the mesenchymal stem cell is an adipose stem cell.

5. The method as claimed in claim 4, wherein the butylidenephthalide (BP) is administered at an amount ranging from 30 mg (as BP)/kg-body weight to 2000 mg (as BP)/kg-body weight per day.

6. The method as claimed in claim 3, wherein the butylidenephthalide (BP) is administered at an amount ranging from 30 mg (as BP)/kg-body weight to 2000 mg (as BP)/kg-body weight per day.

7. The method as claimed in claim 2, wherein the mesenchymal stem cell is an adipose stem cell.

8. The method as claimed in claim 2, wherein the butylidenephthalide (BP) is administered at an amount ranging from 30 mg (as BP)/kg-body weight to 2000 mg (as BP)/kg-body weight per day.

9. The method as claimed in claim 7, wherein the butylidenephthalide (BP) is administered at an amount ranging from 30 mg (as BP)/kg-body weight to 2000 mg (as BP)/kg-body weight per day.

10. The method as claimed in claim 1, wherein the mesenchymal stem cell is an adipose stem cell.

11. The method as claimed in claim 10, wherein the butylidenephthalide (BP) is administered at an amount ranging from 30 mg (as BP)/kg-body weight to 2000 mg (as BP)/kg-body weight per day.

12. The method as claimed in claim 1, wherein the butylidenephthalide (BP) is administered at an amount ranging from 30 mg (as BP)/kg-body weight to 2000 mg (as BP)/kg-body weight per day.

* * * * *